United States Patent [19]
Santoro et al.

[11] Patent Number: 5,932,693
[45] Date of Patent: Aug. 3, 1999

[54] ANTITHROMBOTIC PEPTIDES

[75] Inventors: Samuel A. Santoro, St. Louis, Mo.; William D. Staatz, Oro Valley, Ariz.

[73] Assignee: Washington University, St. Louis, Mo.

[21] Appl. No.: 08/982,597

[22] Filed: Dec. 2, 1997

Related U.S. Application Data

[60] Provisional application No. 60/032,542, Dec. 10, 1996.

[51] Int. Cl.$^6$ ...................................................... C07K 5/20
[52] U.S. Cl. ........................ 530/326; 530/327; 530/328; 530/329; 514/14; 514/15; 514/16
[58] Field of Search ................... 530/326, 327, 530/328, 329; 514/14, 15, 16

[56] References Cited

U.S. PATENT DOCUMENTS

| | | | |
|---|---|---|---|
| 4,517,686 | 5/1985 | Ruoslahti et al. | 3/1 |
| 4,578,079 | 3/1986 | Ruoslahti et al. | 623/11 |
| 4,589,881 | 5/1986 | Pierschbacher et al. | 623/11 |
| 4,857,508 | 8/1989 | Adams et al. | 514/18 |
| 5,120,830 | 6/1992 | Santoro | 530/327 |

FOREIGN PATENT DOCUMENTS

WO90/13653  11/1990  WIPO.

OTHER PUBLICATIONS

Winters, et al., *Chemical Abstracts* 119:5674, July 5, 1993.
Kornblitt, et al., *Chemical Abstracts* 103:15515, Nov. 17, 1985.
Mohri et al., *Chemical Abstracts* 122: 23611, May 8, 1995.
Winters, et al., *Blood*, vol. 81, No. 7, 1993; pp. 1778–1786.
Staatz et al., *J. Biol. Chem.* vol. 266, 1991; pp. 7363–7367.
Hynes, *Cell*, vol. 69, 1992; pp. 11–25.
Piotrowicz et al., *J. Cell Biol.*, vol. 106, 1988; pp. 1359–1373.
Haverstick et al., *Blood*, vol. 66, 1985; pp. 946–953.

*Primary Examiner*—Cecilia J. Tsang
*Assistant Examiner*—Anism Gupta
*Attorney, Agent, or Firm*—Scott J. Meyer

[57] ABSTRACT

Novel short peptides are disclosed which are selected from the group consisting of TAVTQTYGGNSNGEP and fragments thereof containing the minimal sequence TAVTQTY. These peptides are antithrombotic agents and mediate divalent cation-independent adhesion of platelets to fibronectin.

10 Claims, 10 Drawing Sheets

```
I-6    ➜ AAVYQPQPHPQPPPYGH [SEQ ID NO:16]

II-1     CVTDSGVVYSVGMQWLKTQGNKQMLCTCLGNGVSCQE [SEQ ID NO:17]

II-1     TAVTQTYGGNSNGEPCVLPFTYNGRTFYSCTTEGRQDGHLWCSTTSNYEQDQKYSFCTDH
                                                        [SEQ ID NO:18]

II-2     TVLVQTQGGNSNGALCHFPFLYNNHNYTDCTSEGRRDNMKWCGTTQNYDADQKFGFCPMAAHEEI
       ➜                                                 [SEQ ID NO:19]
       ➜
I-7      CTTNEGVMYRIGDQWDKQHDMGHMMRCTCVGNRGEWTCYAYSQLRDQ [SEQ ID NO:20]

I-8      CIVDDITYNVNDTFHKRHEEGHMLNCTCFGQGRGRWXCDPVDQ [SEQ ID NO:21]

I-9      CQDSETGTFYQIGDSWEKYVHGVRYQCYCYGRGIGEWHCQPLQTYPSS [SEQ ID NO:22]
```

➜ Potential thermolysin cleavage sites
<u>R</u> Arg336 and Arg346

Fig. 3

| PEPTIDE | SEQUENCE |
|---|---|
| II-1 | TAVTQTYGGNSNGEPCVLPFFTYNGR̲TFYSCTTEGRQDGHLWCSTTSNYEQDQKYSFCTDH [SEQ ID NO:18] |
| FN312-326 | TAVTQTYGGNSNGEP [SEQ ID NO:1] |
| FN316-333 | QTYGGNSNGEPS̲VLPFFTYNGR̲TFY [SEQ ID NO:23]<br>　　　　　　　C |
| FN330-346 | PFFTYNGR̲TFYS̲TTEGR̲ [SEQ ID NO:24]<br>　　　　　　C |
| FN342-353 | TTEGR̲QDGHLWS̲ [SEQ ID NO:25]<br>　　　　　C |
| FN352-368 | S̲STTSNYEQDQKYSFS̲ [SEQ ID NO:26]<br>C　　　　　　　　　C |

R̲ Arg336 and Arg346
S̲ Ser residues substituted for Cys resdues during synthesis

ANTITHROMBOTIC PEPTIDES

This application claims the benefit of provisional Application Ser. No. 60/032,542, filed Dec. 10, 1996.

The invention herein was made in part with government support under grant number HL49082 by the National Heart, Lung and Blood Institute and by a grant from Monsanto Company.

BACKGROUND OF THE INVENTION

The present invention relates to novel antithrombotic peptides and, more particularly, to short peptides that mediate divalent cation-independent adhesion of platelets to fibronectin. These peptides recognize and/or inhibit adhesion in the first type II (type II-1) repeat element of fibronectin. This repeat element exists in the 45 kDa gelatin-binding domain of fibronectin.

NOTE: Literature references on the following background information and on conventional test methods and laboratory procedures well-known to the ordinary person skilled in the art, and other such state-of-the-art techniques as used herein, are indicated by reference numbers in parentheses, and appended at the end of the specification.

Fibronectin (FN) is a large glycoprotein which is found in plasma and extracellular matrices and is associated with cell membranes where it has been shown to play an important role in mediating the adhesive properties of platelets and other cell types (for reviews, see references 1 and 2). The FN molecule is composed of a series of repeat elements, which are grouped linearly along the polypeptide chain to form functional domains (see FIG. 1). Several of these domains have been implicated in the adhesive activities of FN.

The pioneering studies of Pierschbacher and Ruoslahti (3) established the critical role of the RGD sequence in mediating the adhesion-promoting properties of the cell-binding domain. More recent studies have indicated that adjacent flanking sequences also contribute to the adhesive properties within this domain (4,5,6). At least two further sequences within the alternately-spliced IIICS repeat (LDV and REDV) may also help mediate adhesive activity for some cell types (7,8).

Furthermore, several studies ((9,10), for example) have implicated at least two sites within the high affinity carboxy terminal heparin-binding domain in promoting cell adhesion to FN, while a site within the amino terminal 27 kDa of FN is thought to interact with the matrix assembly receptor (11,12). Clearly the interactions of cells with FN are complex and may be mediated by a variety of receptors interacting with distinct sites on the FN molecule.

An early response to vascular injury is the deposition of platelets on the exposed subendothelial surface. Under the conditions of flow, this deposition has been shown to depend upon the presence of both FN and von Willebrand Factor (13,14,15). In simpler model systems, FN has been shown to be necessary for platelet deposition onto collagenous substrates (16), and under static conditions FN has been shown to mediate platelet spreading on collagen substrates (17,18).

To date only two FN receptors have been identified on platelet surfaces, the $\alpha_5\beta_1$ integrin (GP Ie-IIa) complexes (19,20). As integrins, both of these receptors require the presence of divalent cations for ligand binding activity (21). In addition, while the $\alpha_{IIb}$-$\beta_3$ complex binds FN, fibrinogen, vitronectin and Von Willebrand Factor, it requires activation to do so (20).

Nievelstein and Sixma (14) studied the FN-dependent adhesion of platelets to collagen-coated surfaces and to the extracellular matrix of cultured endothelial cells under conditions of flow. On the basis of experiments with RGD-containing peptides, which inhibit both $\alpha_5\beta_1$ and $\alpha_{IIb}\beta_3$ function, platelets from patients with Glanzmann's thrombasthenia, which lack $\alpha_{IIb}\beta_3$, and inhibitory antibodies directed against the $\alpha_{IIb}\beta_3$ and $\alpha_5\beta_1$ integrins, they concluded that there must exist yet another "binding system" on platelets for FN which is operational when FN is adsorbed onto a surface.

Fibronectin has been shown to in fact undergo a conformational change upon adsorption onto surfaces and this change results in exposure of initially cryptic determinants (22,23). Previous studies by the present inventor and his group and by Piotrowicz et al (19, 24) indicated that 20–50% of total platelet adhesion to FN in a static system was resistant to inhibition by either EDTA or by a combination of saturating concentrations of antibodies directed against the $\alpha_{IIb}\beta_3$ and $\alpha_5\beta_1$ integrins, further substantiating the presence of an additional adhesive mechanism.

Recently, Winters et al (25) demonstrated that the divalent cation-independent adhesion of platelets to FN is mediated by the 45 kDa gelatin-binding domain, which is released from FN by digestion with thermolysin. Unlike the $\alpha_5\beta_1$ integrin-mediated-, divalent cation-dependent platelet adhesion which leads to extensive platelet spreading, this gelatin-binding domain supported-, divalent cation-independent platelet adhesion does not support the spreading of platelets on FN-coated substrates.

Furthermore, this divalent cation-independent adhesion is resistant to either reduction and alkylation nor by enzymatic deglycosylation of the 45 kDa domain. Neither peptides containing the RGD- or the DGEA-sequences nor inhibitory antibodies directed against the $\alpha_{IIb}\beta_3$, $\alpha_v\beta_3$, $\alpha_2\beta_1$ and $\alpha_5\beta_1$ integrins, the GPIb-IX complex (Von Willebrand factor receptor) or against thrombospondin inhibited the divalent cation-independent adhesive mechanism.

These results indicate that platelets have an adhesive system, which permits them to adhere to the gelatin-binding domain of FN in a divalent cation-independent manner, and that the recognition site for the receptor(s) mediating this mechanism appears to consist of a linear polypeptide sequence within the 45 kDa gelatin-binding domain of FN. Accordingly, it is an object of this invention to determine the minimal sequence of amino acids constituting the adhesion recognition site for this mechanism.

BRIEF DESCRIPTION OF THE INVENTION

In accordance with the present invention, novel synthetic peptides are provided which are useful antithrombotic agents. These peptides mediate divalent cation-independent adhesion of platelets to fibronectin. They recognize and/or inhibit adhesion in the first type II (type II-1) repeat element of fibronectin (FN). This repeat element exists in the 45 kDa gelatin-binding domain of fibronectin.

These peptides preferably are selected from the group consisting of TAVTQTYGGNSNGEP [SEQ ID NO:1] and fragments thereof containing the minimal sequence TAVTQTY [SEQ ID NO:2]. While the sequence, TAVTQTY, is important for recognition of the peptide, some of the succeeding five amino acids in GGNSNGEP [SEQ ID NO: 10], are required for peptide binding to the receptor. Removal of the C-terminal GEP from this peptide reduces the apparent affinity of the peptide but does not abolish its ability to inhibit divalent cation-independent platelet adhesion to the 45 kDa gelatin-binding domain of fibronectin.

The foregoing peptides are shown by the required 37 CFR §1.821–1.825 three-letter symbols in the appended Sequence Listing as follows:

```
Thr Ala Val Thr Gln Thr Tyr Gly Gly Asn Ser Asn Gly Glu Pro.      [SEQ ID NO:1]
1           5               10              15

Thr Ala Val Thr Gln Thr Tyr.                                       [SEQ ID NO:2]
1           5

Thr Ala Val Thr Gln Thr Tyr Gly.                                   [SEQ ID NO:3]
1           5

Thr Ala Val Thr Gln Thr Tyr Gly Gly.                               [SEQ ID NO:4]
1           5

Thr Ala Val Thr Gln Thr Tyr Gly Gly Asn.                           [SEQ ID NO:5]
1           5               10

Thr Ala Val Thr Gln Thr Tyr Gly Gly Asn Ser.                       [SEQ ID NO:6]
1           5               10

Thr Ala Val Thr Gln Thr Tyr Gly Gly Asn Ser Asn.                   [SEQ ID NO:7]
1           5               10

Thr Ala Val Thr Gln Thr Tyr Gly Gly Asn Ser Asn Gly.               [SEQ ID NO:8]
1           5               10

Thr Ala Val Thr Gln Thr Tyr Gly Gly Asn Ser Asn Gly Glu.           [SEQ ID NO:9]
1           5               10

Gly Gly Asn Ser Asn Gly Glu Pro.                                   [SEQ ID NO:10]
1           5
```

As described herein, peptide fragments and synthetic peptides have been used to identify the minimum sequence of amino acids constituting the adhesion recognition site for the receptor(s) mediating the adhesive system whereby platelets adhere to the 45 kDa gelatin-binding domain of FN. It is also shown herein that the divalent-cation-independent adhesion mechanism is restricted to platelets and cells of megakaryocytic origin.

The peptides described herein can be prepared by isolation of fibronectin fragments and by conventional solution and solid phase peptide synthesis and peptide sequencing methods well-known to the person skilled in the art.

It will be understood that conservative substitutions of the component amino acids, and additions or deletions at the termini of these peptides, which do not adversely or detrimentally affect their biologic activity as defined herein are meant to be included within the scope of the invention as claimed herein.

DETAILED DESCRIPTION OF THE INVENTION

While the specification concludes with claims particularly pointing out and distinctly claiming the subject matter regarded as forming the present invention, it is believed that the invention will be better understood from the following preferred embodiments of the invention taken in conjunction with the accompanying drawings.

BRIEF DESCRIPTION OF THE DRAWINGS

FIG. 2, in two parts, 2A and 2B, shows that platelets adhere to 45 kDa and 28 kDa gelatin-binding fragments of fibronectin in a divalent cation-independent manner. Fibronectin was digested with thermolysin and then passed over a gelatin-SEPHAROSE column.

FIG. 3 shows the amino acid sequence of the 45 kDa gelatin-binding fragment of fibronectin. The sequence is divided into type I- and type II repeat elements, according to the convention of Kornblihtt et al. (28). The thermolysin cleavage site at $Ala_{261}$ and the proposed thermolysin cleavage sites in repeat I-7 are indicated by arrows (↓) and the cleavage sites for clostripain at $Arg_{338}$ are underlined (R).

FIG. 4 in two parts, 4A and 4B, shows identification of peptides from a clostripain digest of the 28 kDa gelatin-binding fragment that support platelet adhesion.

FIG. 6 shows the amino acid sequences of synthetic peptides and their relative locations along the second type II repeat element of FN. Peptide names include the numbers of the first and last amino acid residue they contain from the mature FN molecule, using the numbering convention of Kornblihtt et al (28). During synthesis, all Cys (C) residues were replaced with Ser (S) residues to prevent disulfide bond formation. Note the positions of the clostripain at $Arg_{336}$- and $Arg_{346}$ residues (R).

FIG. 7, in two parts, 7A and 7B, shows that the peptide, $FN_{312-326}$, specifically inhibits platelet adhesion to the 45 kDa gelatin-binding fragment of fibronectin.

The platelets were then permitted to adhere to the relevant substrates in the continued presence of those cations for 60 min before the nonadherent platelets were washed away and the adherent platelets quantitated as described in the Methods, below. The data are represented as the mean±S.D. of three separate measurements for each condition.

Figure 8:
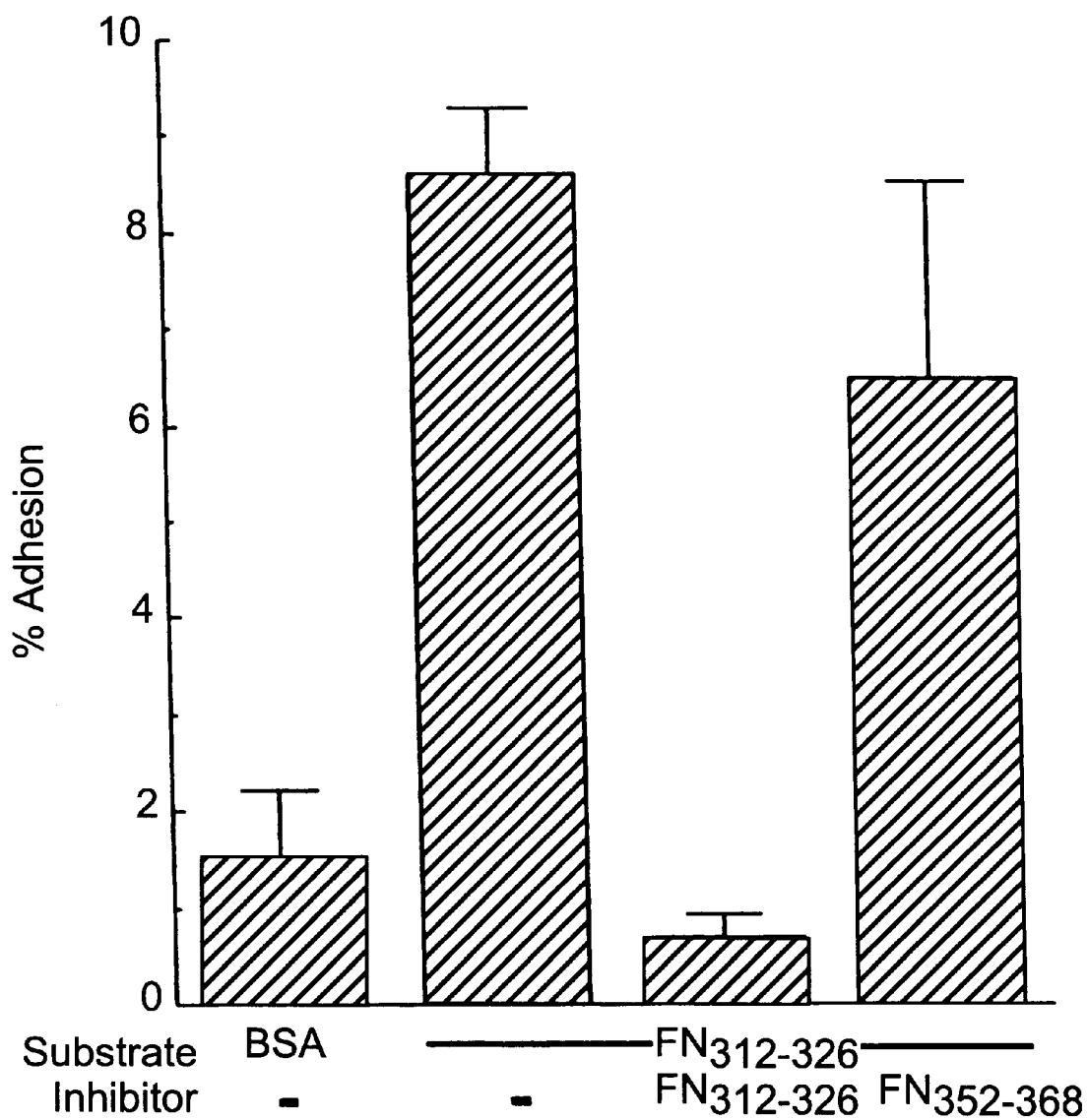

FIG. 8 shows percent (%) adhesion for substrate in which substrates composed of $FN_{312-327}$ cross-linked to BSA support the divalent cation-independent adhesion of platelets. The peptide, $FN_{312-327}$, was cross-linked to BSA coated onto wells, using Sulfo-MBS. The wells were then blocked with 0.5% BSA for use as adhesion substrates, as described in Materials and Methods, below.

Platelets adhered to this substrate in the presence of 2 mM EDTA and this adhesion was inhibited by preincubating the platelets in 300 μM concentrations of $FN_{312-326}$ for 330 min prior to placing them on adhesion substrates. Comparable concentrations of $FN_{352-368}$ have no significant effect on platelet adhesion. These data are presented as the mean±S.D. of three separate measurements for each condition.

In order to illustrate the invention in further detail, the following specific laboratory examples were carried out. Although specific examples are thus illustrated herein, it will be appreciated that the invention is not limited to these specific, illustrative examples or the details therein.

EXAMPLES

MATERIALS AND METHODS

Materials

Gelatin SEPHAROSE and SEPRACRYL S-200 were purchased from Pharmacia, (Piscataway, N.J.). Acrylamide was obtained from Amaresco (Solon, Ohio). Outdated human plasma was obtained from the blood bank at Barnes Hospital, St. Louis, Mo. Tissue culture media and sera were obtained from Gibco-BRL, Grand Island, N.Y. Immulon II 96-well plates came from Dynatech Labs, Chantilly, Va. Synthetic peptides were purchased from Genosys, Woodlands, Tex. Peptide names indicate the amino acid residues from the mature fibronectin molecule which are included in each peptide. Thermolysin, prostaglandin $E_1$ ($PGE_1$), EDTA, leupeptin, aprotinin, phenylmethylsulfonyl fluoride (PMSF), and sodium dodecyl sulfate (SDS) came from Sigma Chemical Co., St. Louis, Mo. Unless specified, all other reagent grade chemicals were purchased from Fisher Scientific, (Pittsburgh, Pa.).

Isolation of Fibronectin Fragments

Human plasma fibronectin was purified from outdated human plasma by affinity chromatography with gelatin-SEPHAROSE followed by size selection on S-200 SEPHAROSE, as described by Ruoslahti et al (26). Purified fibronectin was dialysed into tris-buffered saline (TBS), pH 7.6, 2.25 mM $CaCl_2$ and cleaved with 6.0 μg/ml thermolysin for 5 hr at room temperature (25). Digestion was stopped by adding EDTA to 5 mM and 45 kDa fragment was isolated by affinity chromatography gelatin-SEPHAROSE followed by size-selection on SEPRAROSE S-200. Alternately, digestions were extended to between 16- and 18 hr, in order to increase the yield of the 28 kDa peptide as described below.

Recombinant FN type II Repeat Peptides

Recombinant FN type II-1 and type II-2 peptides were produced and purified as described to previously (27). The rII-1 peptide included amino acid residues 312 to 371 of the mature FN molecule, while rII-2 contained residues 372 to 431, using the convention of Kornblihtt, et al (28).

Electrophoresis

Polyacrylamide gel electrophoresis (SDS-PAGE) was carried out in the presence of sodium dodecyl sulfate (29) and proteins were detected by staining with Coomassie Blue. Proteins and peptides were electrophoretically transferred (Western Blotted) onto polyvinyl difluoride (PVDF) (30).

Platelet- and Cell Adhesion

Adhesion substrates were prepared by coating 100 μl aliquots of fibronectin or the desired peptides onto separate wells of a 96-well Immulon II microliter plate (Dynatech, Chantilly, Va.) as described previously (25). Briefly, wells were coated overnight at 4° C. with protein concentrations of 10–50 μg/ml in 0.05M Tris-HCl, 0.15M NaCl, pH 7.4 (TBS). After coating, non-specific protein-binding sites were then blocked for 2 h with 0.5% BSA at room temperature.

Washed platelets were prepared as described previously (31), and 100 μl of platelet suspension were permitted to adhere to the substrates in each well (25,31). In some cases, platelets were incubated with various concentrations of peptides for 30 min before being added to the substrates. Unless otherwise specified, adhesion was carried out for 60 min at room temperature, after which the non-adherent platelets were removed by gentle washing. Platelet adhesion was then quantitated by measuring their hexose aminidases activity (10,25).

Peptide Sequencing

Proteins were separated by SDS-PAGE on 10% gels and transferred by Western blot to PVDF membranes. After the membranes were stained with amido black, the desired bands were excised and their amino-terminal sequences were determined by standard protocols at the Protein Chemistry Core Facility at Washington University, St. Louis, Mo.

Gel Filtration Chromatography

Peptides were dissolved in a minimum volume of TBS containing 2M guanidine hydrochloride. 50–100 μl aliquots were loaded onto a 1×28 cm SEPHAROSE-12 column and fractionated by FPLC (Pharmacia, Piscataway, N.J.) at a flow rate of 0.4 ml/min, with absorbance being monitored at 280 nm. Molecular weights were computed using BSA (68 kDa), ovalbumin (43 kDa), carbonic anhydrase (29 kDa), cytochrome C (17 kDa) and aprotinin (6500 kDa) as standards.

Peptide Cross-linking

Since amino acid residue 327 of the FN molecule is cysteine, the sulfhydryl-reactive cross-linking reagent, m-maleimedobenzoyl-N-hydroxysulfosuccinimide ester (Sulfo-MBS), was used to cross-link the peptide $FN_{312-327}$, to BSA coated onto the surfaces of 96-well plates. Wells of 96-well plates were coated with 100 μl of 0.5% BSA in 5.3 mM KCl, 0.44 mM $KH_2PO_4$, 137 mM NaCl, 4.16 mM $NaHCO_3$, 0.30 mM $Na_2HPO_4$, 5.6 mM glucose EDTA, pH 7.5 (HBSS-E) overnight at 4° C. After washing the wells five times with 200 μl of 1 mM $FN_{312-327}$ in HBSS-E after which the wells were emptied and the reaction quenched with 200 μl TBS and blocked with 0.5% BSA in TBS, as described above, before being used as adhesion substrates.

Cell Culture

MDCK cells, 54.K cells and 55.K cells and Mm5MT cells were obtained from the American Type Culture Collection (ATCC, Rockville, Md.) and were grown in Dulbecco's modified Eagle's medium (DMEM) containing 10% fetal bovine serum (FBS). NMuMG cells were a gift from Dr. Stanley Korsemeyer (Washington University) and were grown in DMEM supplemented with 10% FBS and 0.1 IU/ml insulin. T-47D cells were obtained from the American Type Culture Collection (ATCC, Rockville, Md.) and were grown in DMEM supplemented with 10% FBS and 0.2 IU/ml insulin. BAE cells were grown in M-199 supplemented with 10% FBS, $10^{-5}$M thymidine. K562 cells were obtained from the ATCC and were grown in RPMI 1640 FBS. All culture media were supplemented with L-glutamine, penicillin and streptomycin. To stimulate K562 cells to enter the megakaryocytic differentiation pathway, cultures were treated with 40 nM phorbol-12,13-dibutyrate for 7–12 days prior to examining their adhesion to the 45 kDa gelatin-binding domain of fibronectin (32).

RESULTS

Figure 1:
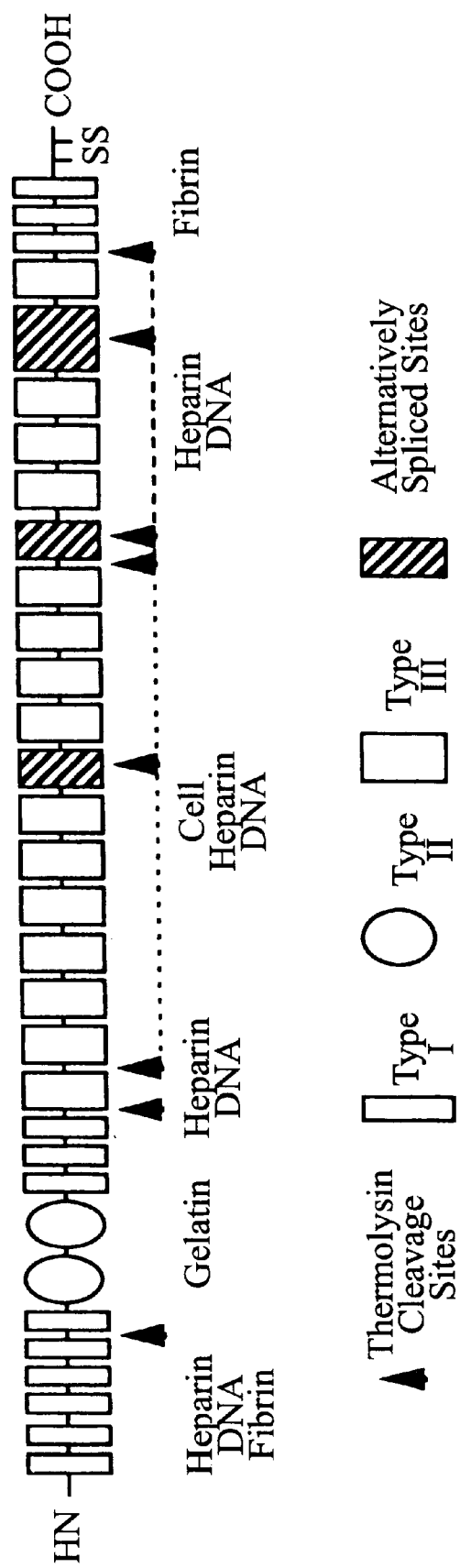
FIG. 1 is a schematic diagram of the fibronectin monomer showing the individual repeat elements and the primary thermolytic cleavage sites. The major thermolysin cleavage sites are indicated by the arrows, while the main ligands of each fragment are also listed below their respective domains.

The fibronectin molecule is composed of a series of conserved repeat elements which are arranged linearly along the polypeptide chain to form functional domains (FIG. 1). Due to the extensive disulfide crosslinking within the fibronectin molecule, digestion of fibronectin with proteases leaves these domains essentially intact and each domain can be isolated in relatively pure form.

The 28 kDa peptide

Figure 2A:
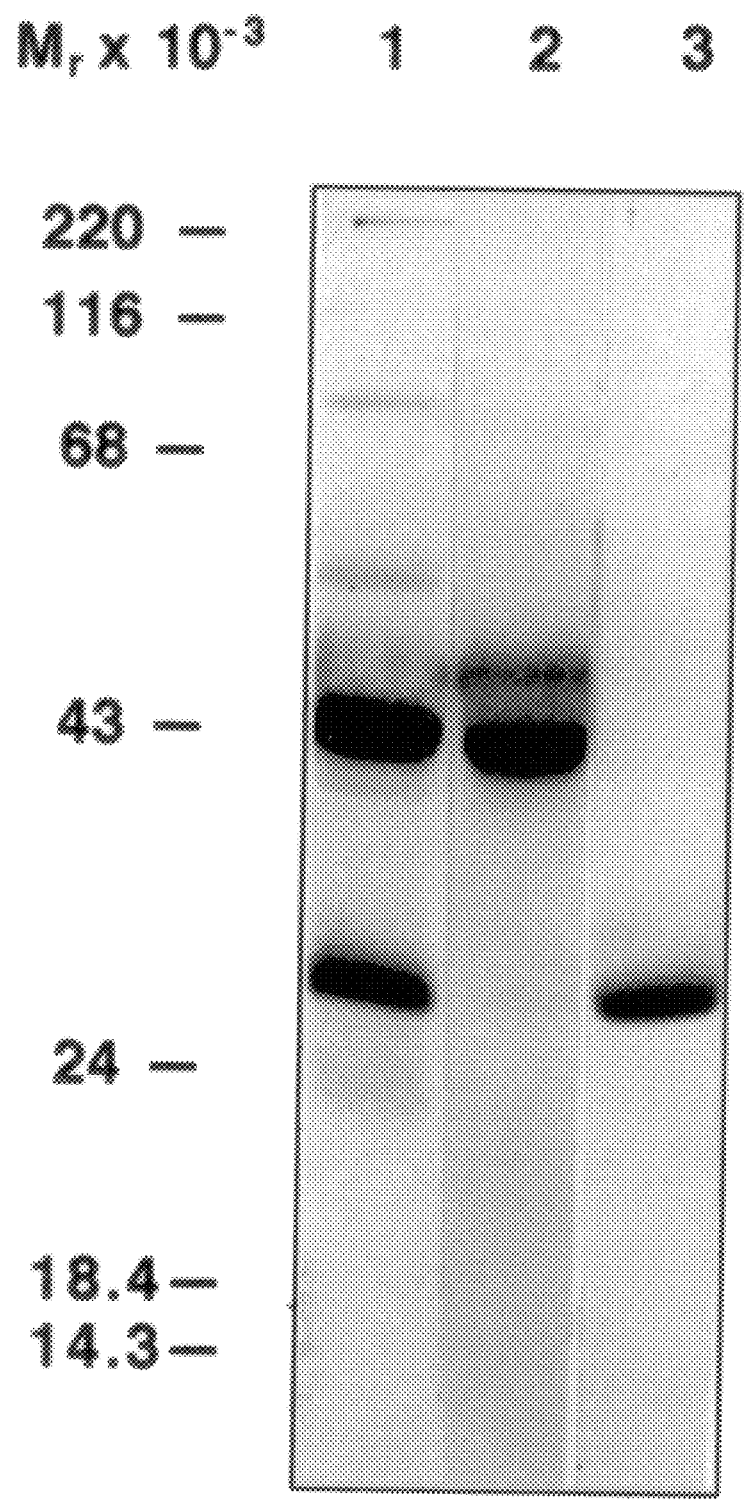
FIG. 2A shows the SDS-PAGE analysis of eluate from a gelatin SEPHAROSE column (lane 1) containing bands at 45 kDa and 28 kDa. The 45 kDa (lane 2) and the 28 kDa (lane 3) peptides after separation by gel filtration on a Sephacrys S-200 column.

Winters et al (25) have previously shown that platelets adhere in a divalent cation-independent manner to 45 kDa peptide released from FN by digestion with thermolysin. During the purification of this 45 kDa peptide from thermolysin digests of FN it was detected that a 28 kDa peptide that co-eluted with 45 kDa from gelatin SEPHAROSE columns (FIG. 2A, lane 1.) Prolonging the digestion time from 5 hr to 16–24 hr significantly increased the amount of this 28 kDa peptide in proportion to 45 kDa peptide recovered and allowed separation of significant quantities of both these peptides by gel filtration on SEPHAROSE S-200 (FIG. 2A, lanes 2 and 3, respectively).

Figure 2B:
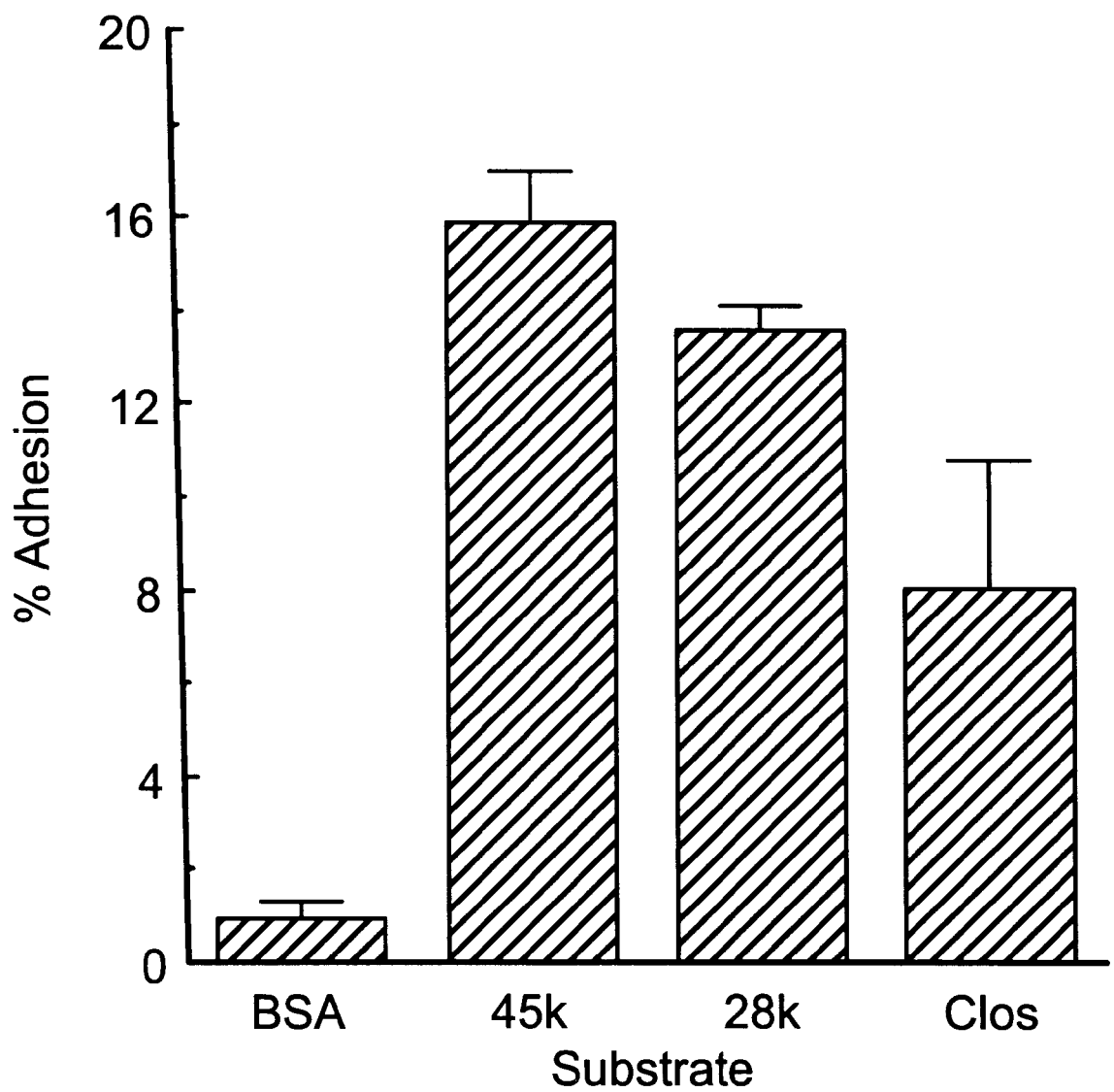
FIG. 2B shows the percent (%) adhesion of substrate in which platelets adhere comparably to both the 45 kDa and the 28 kDa gelatin-binding fragments of fibronectin in the presence of 2 mM EDTA. In addition, they also adhere to clostripain (clos) digests of the 28 kDa fragment. These data represent the means±S.D. of three separate measurements of platelet adhesion.

When adhesion substrates were prepared from 45 kDa and 28 kDa, it was found that platelets adhered in a divalent cation-independent manner to a comparable extent on both the 45 kDa and the 28 kDa peptides (FIG. 2B). Because of the similarity in the adhesive abilities of these two peptides, samples of each peptide were submitted to amino-terminal sequence analysis. The results indicate that both 45 kDa and 28 kDa peptides begin with AVYQPQPHPQP [SEQ ID NO: 11]. Thus 28 kDa represents approximately 62% of the amino-terminus of 45 kDa (FIG. 3). The most likely carboxy-terminal cleavage site of 28 kDa peptide should, therefore, lie at the end of the second type II repeat or in the first half of the seventh type I repeat element.

Clostripain Digests of 28 kDa Peptide

In order to more narrowly define the region within 28 kDa which supports divalent cation-independent platelet adhesion, aliquots of this peptide were reduced and alkylated and then digested with sequencing grade clostripain. Adhesion substrates made from these digests supported divalent cation-independent platelet adhesion, albeit not as well as did the intact 45 kDa or 28 kDa (FIG. 2B).

Figure 4A:
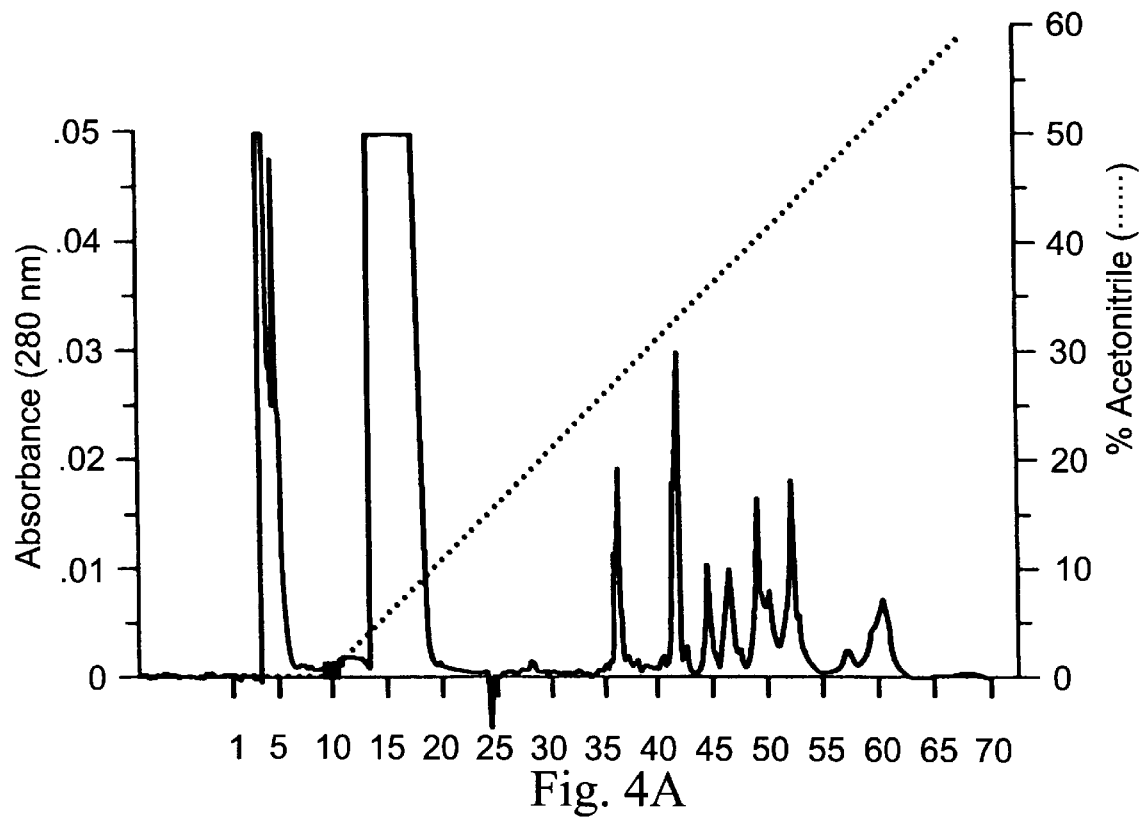
FIG. 4A shows the reverse-phase HPLC separation of a digest using a 0– to 60% acetonitrile gradient (dotted line and left y-axis) yielded multiple peptide peaks (solid line and right y-axis).

When the clostripain digests were fractionated by HPLC, using a C-8 reverse phase column eluted with acetonitrile gradient, the vast majority of the digestion products eluted from the column at acetonitrile concentrations below 10% (FIG. 4A). The remaining peptides, however, eluted from the column as a series of discrete peaks between 25% and 53% acetonitrile. No further material was recovered by washing the column with acetonitrile concentrations between 60% and 100%.

Figure 4B:
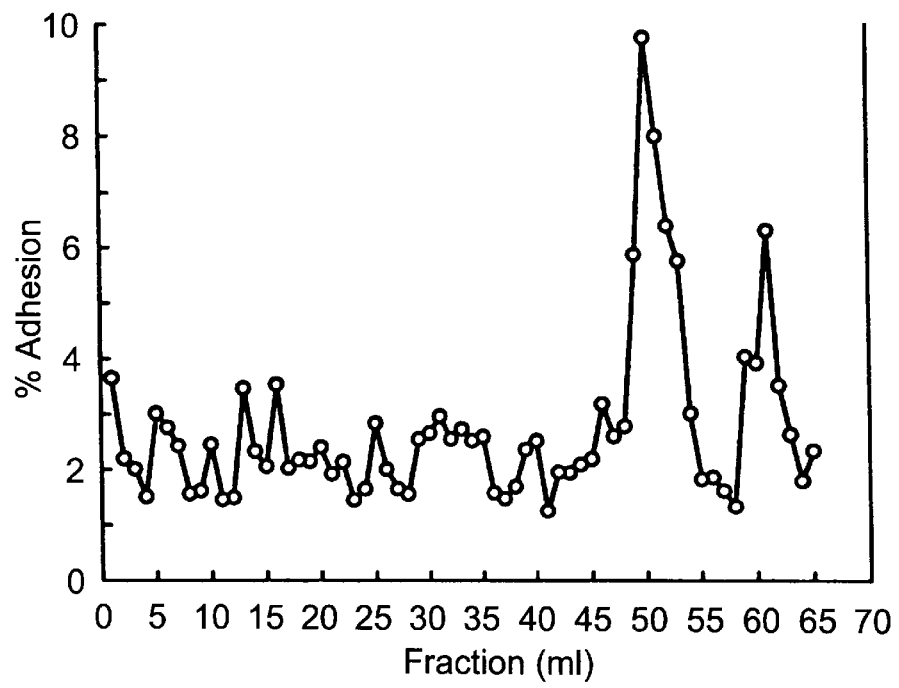
FIG. 4B shows that substrates derived from the HPLC fractions in FIG. 4A supported two peaks of platelet adhesion, with maximal adhesion to fractions 50, which elutes between 39.5% and 40.5% acetonitrile, and 61, which elutes between 49.5% and 50.5% acetonitrile. These data represent the average of two estimates of platelet adhesion.

Over the course of several experiments, adhesion substrates made from these HPLC column fractions always supported divalent cation-independent platelet adhesion to a peak of material which eluted between 50% and 52% acetonitrile (FIG. 4B). This peak in adhesive activity corresponds to the final peptide peak eluted from the column, as detected by absorbance at 280 nm (compare fractions 59–62 in FIGS. 4A and 4B). In the experiment presented in FIGS. 4A and 4B, however, platelets also adhered to a second defined peak of activity centered around 40% acetonitrile (compare fractions 49–52 in FIGS. 4A and 4B).

When amino-terminal sequencing was performed on fractions eluting at 51% acetonitrile from two experiments, the sequence, AVYQPQPHPQP, [SEQ ID NO: 11], was obtained for both samples. Thus, the peptides eluting in 51% acetonitrile have the same amino-terminal sequence as both 45 kDa and 28 kDa. In contrast, amino-terminal sequence analysis from the material shown as fraction 50 in FIG. 4, which eluted at 39.5–40.5% acetonitrile, yielded the sequence, QMLCTCLGNGV [SEQ ID NO: 12]. Thus, although clostripain usually cleaves polypeptides after arginine residues, the peptide in the peak, which eluted at about 40% acetonitrile, was produced by the (rare) cleavage of the 28 kDa polypeptide chain after residue $Lys_{296}$.

While enough material could not be recovered from the peak that eluted between 39.5–40.5% acetonitrile (fraction 50) for further analysis, gel filtration chromatography on SUPEROSE 12 was used to provide molecular weight estimates from several samples of clostripain-derived peptides that eluted between 51% and 52% acetonitrile. These measurements yielded molecular weight estimates ranging from 8,500 Da to 10,300 Da which is consistent with presence of peptides formed by the cleavage of the 28 kDa peptide after $Arg_{336}$, or, in the less likely event of incomplete cleavage by clostripain, after $Arg_{346}$. Both of these residues lie within the amino-terminal half of the first type II repeat element (see FIGS. 3 and 6). For comparison, measurements on two separate preparations of the 28 kDa peptide yielded molecular weight estimates of 28,400 Da, which confirms the molecular weight estimate derived from SDS-PAGE.

The r-Type II Repeats

Figure 5:
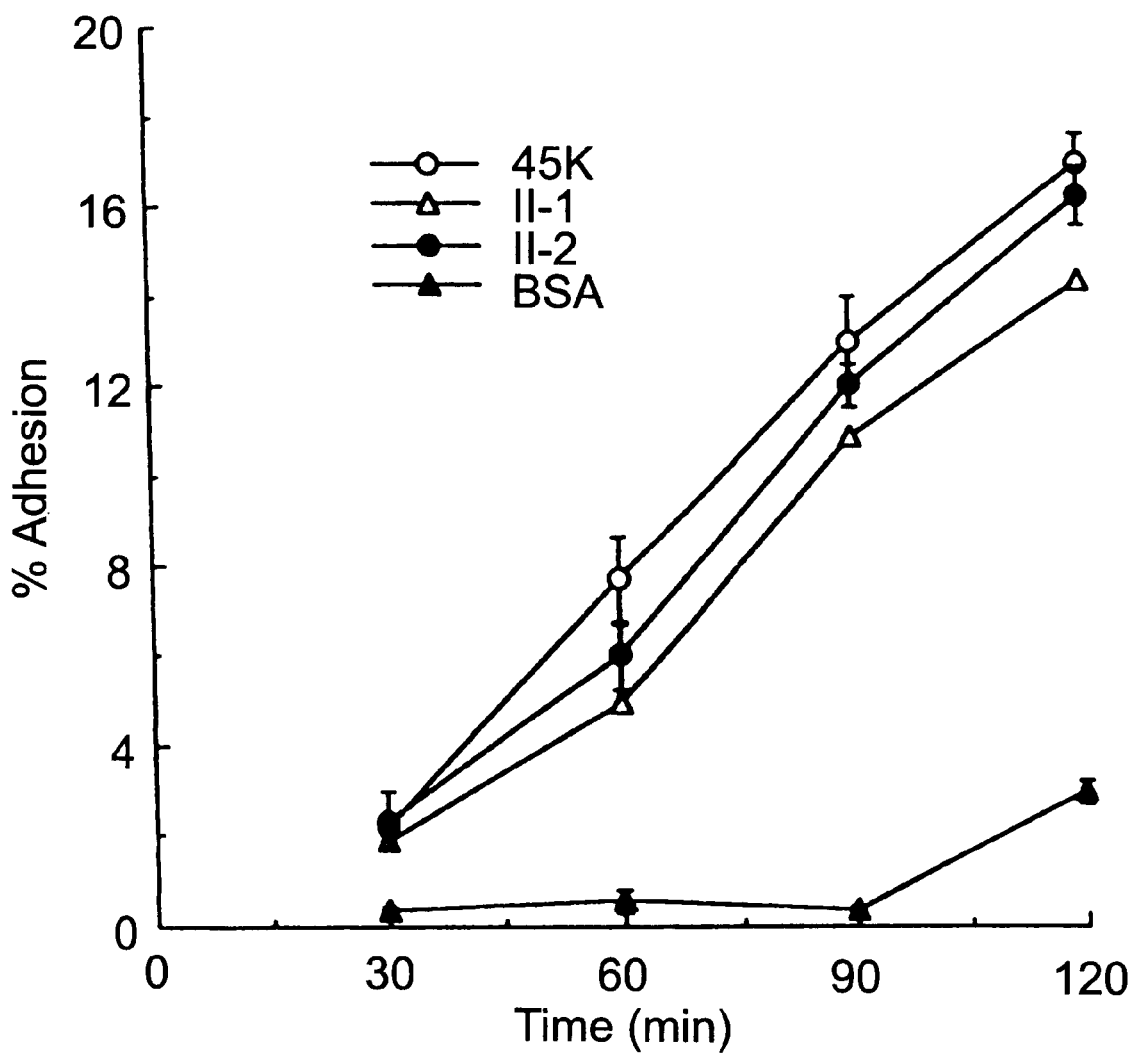
FIG. 5 shows percent (%) adhesion over time in minutes in which platelets adhere to recombinant forms of each type II repeat element. Plates were coated with 50 μl of recombinant peptide at 70 μg/ml. Control substrates were coated with 45 kDa gelatin-binding fragment of fibronectin at 50 μg/ml and with 0.5% BSA. The wells were then blocked with 0.5% BSA and platelets were then permitted to adhere for the times indicated. Each point represents the mean±S.D. of three separate measurements for each time point.

The data from the clostripain digests of 28 kDa suggest that a site within the first type II repeat element may support the divalent cation-independent adhesion of platelets. To examine this possibility, separate wells were coated with recombinant forms of the first- and second type II repeats of fibronectin and platelets were permitted to adhere to them for various times from 30 min to 2 hr in the presence of 2 mM EDTA. As shown in FIG. 5, platelets adhered to each recombinant peptide as well as they did to 45 kDa substrates and this adhesion continued to increase linearly for at least 2 hr. Thus, each sequence type II repeat contains a sequence capable of supporting divalent cation-independent platelet adhesion.

Synthetic Peptides

By combining the known sequence of the recombinant type II-1 repeat (FIGS. 3 and 6) with the predicted carboxy-termini of the active peptides from the clostripain digests, the amino acid sequence from $Thr_{312}$ to $Arg_{346}$ of the intact FN molecule was identified as a region containing at least one sequence which should support the divalent cation-independent adhesion of platelets. A set of overlapping synthetic peptides which spanned most of the type Ii-1 sequence (FIG. 6) were therefore synthesized.

The peptides are named to indicate the amino acid residues of the mature plasma FN sequence (28) contained in each peptide. Furthermore, in order to prevent inappropriate formation of disulfide bonds, all cysteine residues in the native sequence were replaced by conservative substitutions of serine residues in the peptides.

Figure 7A:
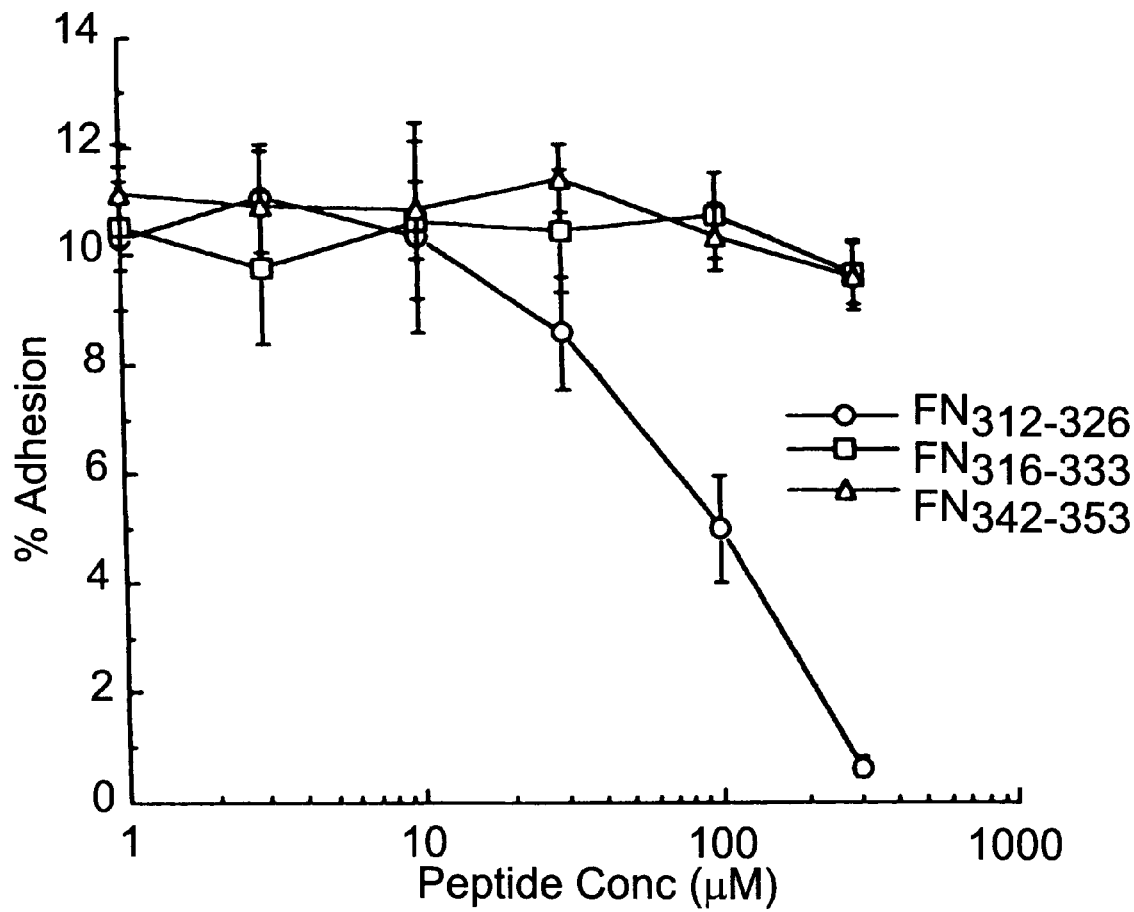
FIG. 7A shows that soluble $FN_{312-326}$ inhibits platelet adhesion to the 45 kDa fragment in a concentration-dependent manner, whereas the control peptides, $FN_{316-333}$ nor $FN_{342-353}$, do not.

When the ability of these synthetic peptides to inhibit the divalent cation-independent adhesion of platelets to substrates composed of 45 kDa was examined, it was found that only peptide $FN_{312-326}$ inhibited this adhesion and that this inhibition occurred in a concentration-dependent manner with half-maximal inhibition occurring at about 68 $\mu$M peptide. Neither $FN_{316-333}$ nor $FN_{342-353}$ had any effect on platelet adhesion (FIG. 7A) and similar negative results were obtained with peptides, $FN_{330-346}$, and $FN_{352-368}$.

Figure 7B:
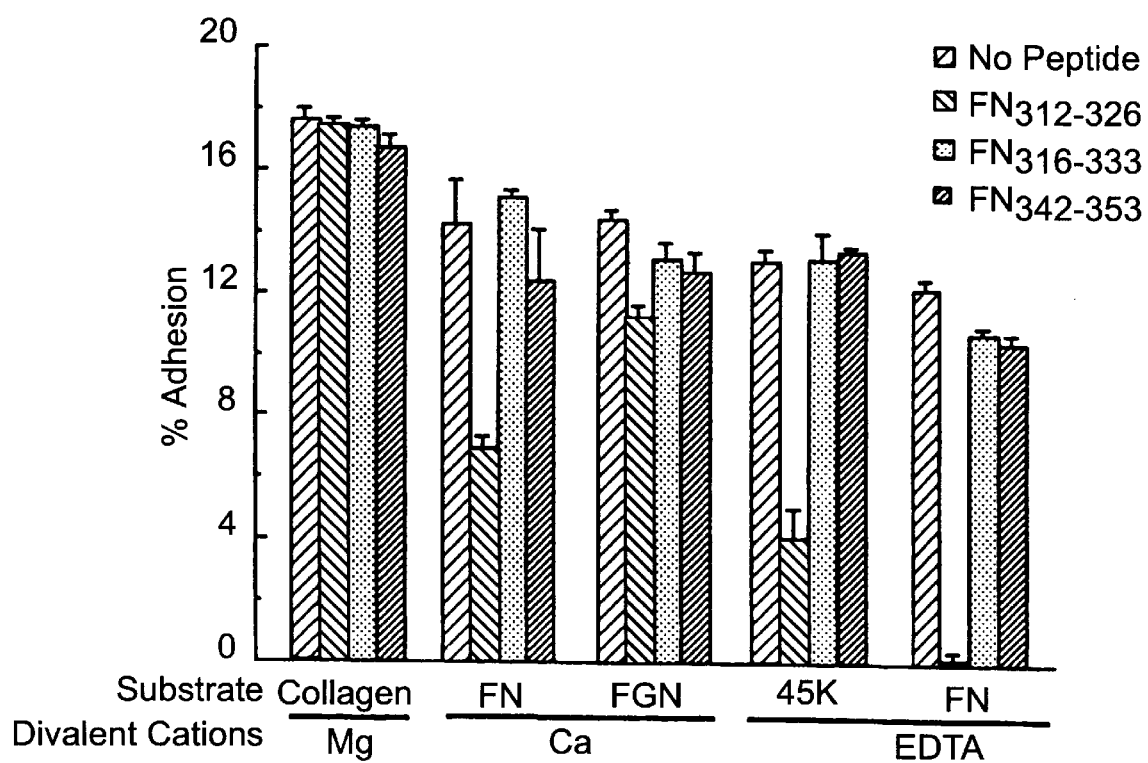
FIG. 7B shows percent (%) adhesion for substrate in which the inhibition of platelet adhesion by $FN_{312-326}$ is specific for substrates composed of fibronectin and the 45 kDa gelatin-binding fragment of fibronectin. Platelets were pre-incubated for 20 min in the presence of 300μ concentrations of either $FN_{312-326}$, $FN_{316-333}$, or $FN_{342-353}$ and the indicated divalent cation (at 2 mM).

To determine the specificity of the inhibitory activity of peptide $FN_{312-326}$, for the divalent cation-independent adhesion of platelets to 45 kDa, washed platelets were incubated in the presence of either $Mg^{+2}$, $Ca^{+2}$ or EDTA and 300 $\mu$M concentrations of either $FN_{312-326}$, $FN_{316-333}$, or $FN_{342-353}$. They were then permitted to adhere for 90 min to substrates composed of either type I collagen, FN, fibrinogen or 45 kDa as shown in FIG. 7B.

In these experiments $FN_{312-326}$ markedly reduced the divalent cation-independent platelet adhesion to 45 kDa and to intact FN and also reduced platelet adhesion to FN by approximately 50% in the presence of $Ca^{+2}$. In contrast, neither $FN_{316-333}$ nor $FN_{342-353}$ inhibited platelet adhesion to FN or to 45 kDa and none of the peptides had any significant effect on divalent cation-dependent platelet adhesion to collagen or fibrinogen. These data are consistent with observations that only about half of the observed platelet adhesion to FN is divalent cation-dependent and suggest that $FN_{312-326}$ may be an important determinant mediating the divalent cation-independent adhesion of platelets.

To test this possibility, the peptide, $FN_{312-327}$, was synthesized. This peptide, while only one amino acid residue longer than $FN_{312-326}$, ends in a Cys residue which allowed use of the sulfhydryl-reactive cross-linking reagent, Sulfo-MBS, to covalent cross-link $FN_{312-327}$ to BSA coated onto wells of 96-well plates.

Platelets readily adhered to these $FN_{312-327}$-BSA conjugates in the presence of 2 mM EDTA (FIG. 8), and this adhesion was inhibited by preincubating the platelets with 300 $\mu$M soluble $FN_{312-326}$ prior to placing them on the adhesive substrates. Preincubating the platelets with $FN_{352-368}$, on the other hand, did not significantly alter their adhesion to the $FN_{312-327}$-BSA conjugate. Thus, it appears that $FN_{312-327}$ is capable of supporting divalent cation-independent platelet adhesion.

Sequences within $FN_{312-326}$ Required for Adhesion

A major difference between the peptides, $FN_{312-326}$ and $FN_{316-333}$, is that $FN_{312-326}$ contains the additional residues, TAVT [SEQ ID NO: 13], at its amino-terminus. Furthermore, while $FN_{312-326}$ appears to mediate the divalent cation-independent adhesion of platelets to 45 kDa, $FN_{316-333}$ has no effect on this adhesion.

To explore the possibility that the adhesive properties of $FN_{312-326}$ are mediated by amino acid residues in the amino-terminal portion of the peptide, two further peptides were synthesized and tested for their abilities to inhibit platelet adhesion to 45 kDa in the absence of divalent cations (FIG. 9).

When tested at concentrations up to 2 mM, the peptide, $FN_{312-318}$, with the sequence TAVTQTY [SEQ ID NO: 2], had little effect on platelet adhesion to 45 kDa. Peptide, $FN_{312-323}$ on the other hand, inhibited this divalent cation-independent adhesion but the concentration at which half-maximal inhibition occurred was approximately 712 $\mu$M, as compared to 68 $\mu$M for $FN_{312-326}$.

These data suggest that amino acid residues in the sequences, TAVT [SEQ ID NO: 13] and GGNSN [SEQ ID NO: 14], are essential for recognition of the peptides by the receptor and that the residues, GEP, at the carboxy-terminus of $FN_{312-323}$ enhance that recognition.

Divalent Cation-independent Adhesion of Cells

While there are numerous reports that many cell lines do not adhere to FN in the absence of divalent cations (for review, see reference 21), platelets do.

It was therefore decided to screen a wide variety of cell types, including cells of megakaryocytic origin, for the ability to adhere to 45 kDa in the presence of 2 mM EDTA. The cell lines tested included both breast- and kidney epithelial lines, primary bovine aortic endothelial cells, fibroblastic kidney cells, the human B-cell lymphoma, Raji, and the pleuripotential human hematopoietic cell line, K562 and the megakaryocytic cell lines, DAMI and MEG-01 (TABLE I).

Both normal and malignant phenotypes are represented in these cells. Since treatment of K562 cells with phorbol esters has been shown to cause them to develop a more megakaryocytic phenotype (32,33), cultures of K562 cells were treated with 40 nM phorbol-12, 13-dibutyrate for 7 to 10 days and then the ability of the cells to adhere to FN and 45 kDa was tested at various intervals between 15- and 90 min.

As shown in Table I, below, aside from platelets, only the two megakaryocytic lines, DAMI and MEG-01, supported significant divalent cation-independent adhesion to substrates composed of either FN or 45 kDa. It is interesting to note that cells in the earlier stages of megakaryocytic development, as represented by the phorbol-treated K562 cells, also failed to adhere to these substrates in the absence of divalent cations. These data suggest that divalent cation-independent adhesion to the 45 kDa gelatin-binding domain of FN may be restricted to platelets and cells which have progressed further along the megakaryocytic developmental pathway.

The foregoing work, which used peptide fragments and recombinant FN type II-1- and type II-2 repeat peptides, shows that there is at least one amino acid sequence in each of the two type II repeat elements of FN which is capable of supporting this divalent cation-independent platelet adhesion. Then, using a series of overlapping synthetic peptides, it is shown that the sequence, TAVTQTYGGNSNGEP [SEQ ID NO:1], which is contained within amino acid residues 312 to 326 of the mature FN molecule, is the recognition sequence for this adhesion in the type II-1 repeat element of FN.

This conclusion is supported by the ability of substrates composed of the peptide, $FN_{312-326}$, cross-linked to BSA to support platelet adhesion in the presence of EDTA and by the ability of soluble $FN_{312-326}$ to inhibit the divalent cation-independent adhesion of platelets to 45 kDa.

Neither the integrin-mediated, $Mg^{+2}$-dependent adhesion of plate-lets to collagen nor the $Ca^{+2}$-dependent adhesion of platelets to fibrinogen is affected by this peptide. Furthermore, $FN_{312-326}$, also appears to be specific in its ability to inhibit the divalent cation-independent component of platelet adhesion to FN, inhibiting only about half of the total platelet adhesion in the presence of $Ca^{+2}$. Neither the peptide, $FN_{312-333}$, which lacks the initial four amino acids, TAVT [SEQ ID NO:13], in the 15-amino-acid-peptide, $FN_{312-326}$, nor the peptide, TAVTQTY [SEQ ID NO:2], which represents the first seven amino acids of $FN_{312-326}$, inhibit platelet adhesion to the 45 kDa gelatin-binding domain of FN.

Thus, while the sequence, TAVTQTY [SEQ ID NO:2], is important for recognition of the peptide, it appears that at least some of the succeeding five amino acids, GGNSNGEP [SEQ ID NO :10], are required for peptide binding to the receptor. Removal of the carboxy-terminal three amino acids, GEP, from $FN_{312-326}$, on the other hand, reduces the apparent affinity of the peptide by approximately 10-fold, compared to the parent peptide but does not abolish its ability to inhibit divalent cation-independent platelet adhesion to 45 kDa. Thus, the entire sequence of $FN_{312-326}$ appears to be necessary for the maximum inhibition of this adhesive process.

An early response to vascular injury is the adhesion and spreading of platelets on the newly exposed subendothelial matrix. In perfusion experiments this adhesive response has been shown to depend upon the presence of FN and von Willebrand factor (13,14). Furthermore, under both flow- (16) and static conditions (17,18), FN has been shown to mediate platelet spreading on collagen substrates. FN has also been shown to mediate the adhesion and spreading of platelets on intact layers of endothelial cells, fibroblasts and smooth muscle layers and their extracellular matrices (16). Platelet adhesion to FN, therefore, plays a crucial role in the initiation of recovery from vascular injury.

While certain types of cells are capable of adhering to the carboxy-terminal heparin-binding domain of FN in the absence of divalent cations (4,10,34), these interactions are thought to be mediated by carbohydrates on the cell surface. The $\alpha_5\beta_1$- and $\alpha_{IIb}\beta_3$ integrin complexes, on the other hand, are well characterized as the receptors responsible for mediating divalent cation-dependent platelet adhesion to FN (21). Yet inhibiting these receptors with combinations of integrin-specific antibodies or with RGD-containing peptides has, at most reduced platelet adhesion to FN by 50- to 65% (14, 19,25).

This led Nievelstein (14) to hypothesize another "binding system" on platelets for FN and it has been shown that this mechanism works in the absence of divalent cations (19,24, 25). In accordance with the present invention, this divalent cation-independent platelet adhesion is mediated by at least one site within each of the two type II repeat elements of FN. The site within the first type II repeat which supports this adhesion is contained within the peptide sequence, TAVTQ-TYGGNSNGEP [SEQ ID NO:1], which represents amino acid residues 312–326 of the mature FN molecule. Moreover, due to sequence conservation between the first- and the second type II repeat elements of FN, the amino acid sequence from residue 372 to 386 of mature FN may serve as a recognition sequence for this adhesive mechanism in the second type II repeat element.

When a wide variety of cells were surveyed for their abilities to adhere to FN and 45 kDa, it was found that, aside from platelets, only the two megakaryocytic cell lines, DAMI and MEG-01, were capable of adhering to these substrates in the absence of divalent cations.

It is interesting to note in this respect that the pleuripotential hematopoietic K562 cells did not adhere to 45 kDa substrate. Burger et al (32) have shown that treatment of K562 cells with phorbol esters leads to the development of megakaryocytic markers, including increased expression of the $\alpha_2\beta_1$ and $\alpha_{IIb}\beta_3$ integrins and the loss of the Leu M1 antigen from the cell surfaces.

However, the induction of megakaryocytic markers by treatment with phorbol esters was not accompanied by increased adhesiveness of 45 kDa substrates (32). Thus, acquisition of this adhesive ability, like the acquisition of activation-dependent ligand binding to the $\alpha_{IIb}\beta_3$ integrin, appears to be a late event in megakaryocytic maturation.

TABLE I, below, shows effects of short peptides on the divalent cation-independent adhesion of platelets to the 45 kDa gelatin-binding domain of FN.

TABLE I

Effects of short peptides on the divalent cation-independent adhesion of platelets to the 45 K Da gelatin-binding domain of FN

| Peptide | Sequence | $ED_{50}$ | |
|---|---|---|---|
| $FN_{312-326}$ | TAVTQTYGGNSNGEP [SEQ ID NO:1] | 68 | µM |
| $FN_{316-333}$ | QTYGGNSNGEPSVLPFTY [SEQ ID NO:15] | >2 | mM |
| $FN_{312-323}$ | TAVTQTYGGNSN [SEQ ID NO:7] | 712 | µM |
| $FN_{312-318}$ | TAVTQTY [SEQ ID NO:2] | >2 | mM |

TABLE II, below, shows divalent cation-independent adhesion of cells to the 45 kDa gelatin-binding fragment of fibronectin.

TABLE II

Adhesion of Cell Lines to the 45K Fragment of Fibronectin

| Cell Line | Cell Type | Adhesion |
|---|---|---|
| MDCK | Dog Kidney Epithellum | − |
| 54.K | Mouse Kidney Epithelium | − |
| 55.K | Mouse Kidney (fibroblastic) | − |
| NMBT | Normal Mouse Breast Epithelium | − |
| C127-I | Mouse Breast CA | − |
| Mm 5-MT | Mouse Breast CA | − |
| T47-D | Human Breast CA | − |
| BEn | Bovine Aortic Endothelium | − |
| Raji | Human B-Cell | − |
| K562 | Human Mono/Myo Stem Cell Leukemia | − |
| K562 (+PMA) | (phorbol-induced megacaryocitic phenotype) | − |
| DAMI | Human Megakaryocytic Leukemia | ++ |
| MEG-01 | Human Megakaryocytic Leukemia | + |
| Platelets | Human, Fresh washed | ++ |

Various other examples will be apparent to the person skilled in the art after reading the present disclosure without departing from the spirit and scope of the invention. It is intended that all such other examples be included within the scope of the appended claims.

REFERENCES

1. Mosher, D. F. *Fibronectin* 1–474 (Academic Press, New York, 1989).

2. Hynes, R. O. *Fibronectins* 1–546 (Springer-Verlag, New York, N.Y., 1990).

3. Pierschbacher, M. D., and Ruoslahti, E. (1984) Cell attachment activity of fibronectin can be duplicated by small synthetic fragments of the molecule. *Nature* 309, 30–33.

4. Ramos, J. W., and DeSimone, D. W. (1996) Xenopus embryonic cell adhesion to fibronectin: Position-specific activation of RGD/synergy site-dependent migratory behavior at gastrulation. *J Cell Biol* 134, 227–240.

5. Obara, M., Kang, M. S., and Yamada, K. M. (1988) Site-directed mutagenesis of the cell-binding domain of human fibronectin: Separable, synergistic sites mediate adhesive function. *Cell* 53, 649–657.

6. Bowditch, R. D., Hariharan, H., Tominna, E. F., Smith, J. W., Yamada, K. M., Getzoff, E. D., and Ginsberg, M. H. (1994) Identification of a novel integrin bindingsite on fibronectin: differential utilization by integrins. *J Biol Chem* 269, 10856–10863.

7. Mould, A. P., and Humphries, M. H. (1991) Identification of a novel recognition sequence for integrin $a_4b_1$ in the COOH-terminal heparin-binding domain of fibronectin. *EMBO J* 10, 4089–4095.

8. Guan, J.-L., and H., H O (1990) Lymphoid cells recognize an alternatively spliced segment of fibronectin via the integrin receptor $a_4b_1$. *Cell* 60, 53–61.

9. Woods, A., McCarthy, B. J., Furcht, L. T., and Couchman, J. R. (1993) A synthetic peptide from the COOH-terminal heparin-binding domain of fibronectin promotes focal adhesion formation. *Molecular Biology of the Cell* 4, 605–613.

10. Haugen, P. K., McCarthy, B. J., Skubitz, A. P. N., Furcht, L. T., and Letourneau, P. C. (1990) Recognition of the A chain carboxy-terminal heparin binding region of fibronectin involves multiple sites: two contiguous sequences act independently to promote neural cell adhesion. *J Cell Biol* 111, 2733–2745.

11. Morla, A., and Ruoslahti, E. (1992) A fibronectin self-assembly site involved in fibronectin matrix assembly: reconstruction in a synthetic peptide. *J Cell Biol* 118, 421–429.

12. McKeown-Longo, P. J., and Mosher, D. F. (1985) Interaction of the 70,000-mol-wt amino-terminal fragment of fibronectin with the matrix assembly receptor of fibroblasts. *J Cell Biol* 100, 364–374.

13. Moon, D. G., Matayoshi, B. M., Weston, L. K., Minnear, F. L., and Kaplan, J. E., (1994) Fibronectin inhibition of platelet thrombus formation in an in vivo porcine model of vascular injury. *Thrombosis Res* 76, 343–351.

14. Nievelstein, P. F. E. M., and Sixma, J. J. (1988) Glycoprotein IIB_IIIA and RGD(S) are not important for fibronectin-dependent platelet adhesion under flow conditions. *Blood* 72, 82–88.

15. Beumer, S., Heijnen, H. F., Ijsseldijk, M. J., Orlando, E., de Groot, P. G., and Sixma, J. J. (1995) Platelet adhesion to fibronectin in flow: the importance of von Willebrand factor and glycoprotein Ib. *Blood* 86, 3452–3460.

16. Nievelstein, P. F. E. M., and de Groot, P. G. (1988a) Interactions of blood platelets with the vessel wall. *Haemostasis* 18, 342–359

17. Grinnell, F., and Hayes, D. G. (1978) Cell adhesion and spreading factor. Similarity to cold insoluble globulin in human serum. *Exp. Cell Res.* 115, 221–229.

18. Hynes, R. O., Ali, I. U., Destree, A. T., Mauntner, V., Perkins, M. E., Senger, D. R., Wagner, D. D., and Smith (1978) A large glycoprotein lost from the surface of transformed cells. *Ann. N.Y. Acad. Sci.* 312, 317–343.

19. Piotrowicz, R. S., Orchekowski, R. P., Nugent, D. J., Yamada, K. M., and Kunicki, T. J. (1988) Glycoprotein Ic-IIa functions as an activation-independent fibronectin receptor on human platelets. *J Cell Biol* 106, 1359–1373

20. Faull, R. J., Du, X., and Ginsberg, M. H. (1994) Receptors on platelets. *Methods Enzymol* 245, 183–194.

21. Hynes, R. O. (1991) Integrins: Versatility, modulation, and signaling in cell adhesion. *Cell* 69, 11–25.

22. Ugarova, T. P., Zamarron, C., Velkich, Y., and Bowditch, R. D. (1995) Conformational transitional transformations in the cell binding domain of fibronectin. *Biochemistry* 34, 4457–4466.

23. Fukai, F., Ohtaki, M., Fujii, N., Yajima, H., Ishii, T., Nishizawa, Y., Mayazaki, K., and Katayama, T. (1995) Release of biological activities from quiescent fibronectin by a conformational change and limited proteolysis by metalloproteinases. *Biochemistry* 34, 11453–11459.

24. Staatz, W. D., Fok, K. F., Zutter, M. M., Adams, S. P., Rodriquez, B. A., and Santoro, S. A. (1991) Identification of a tetrapeptide recognition sequence for the a2b1 integrin in collagen. *J. Biol. Chem.* 266, 7363–7367.

25. Winters, K. J., Walsh, J. J., Rubin, B. G., and Santoro, S. A. (1994) Platelet interactions with fibronectin: divalent cation-independent platelet adhesion to the gelatin-binding domain of fibronectin. *Blood* 81, 1778–1786.

26. Ruoslahti, E., Hayman, E. G., Pierschbacher, M., and Engvall, E. (1982) Purification, immunochemical properties, and biological activities. *Methods Enzymol* 82, 803–831.

27. Skorskengaard, K., Holtat, T. L., Etzcrodt, H., and Thogersen, H. C. (1994) Collagen-binding recombinant fibronectin fragments containing type II domains. *FEBS Letters* 343, 47–50.

28. Kornblihtt, A. R., Umezawa, K., Vibe-Pedersen, K., and Baralle, F. E. (1985) Primary structure of fibronectin: differential splicing may generate at least 10 polypeptides from a single gene. *EMBO J* 4, 1755–1759.

29. Laemmli, U. K. (1970) Cleavage of structural proteins during the assembly of the head of bacteriophage T4. *Nature* 227, 860–865.

30. Gooderham, K. (1984) in *Proteins* (Walker, J. M., ed.), pp. 165–178, Humana Press, Clifton, N.J.

31. Haverstick, D. M., Cowan, J. F., Yamada, K. M., and Santoro, S. A. (1985) Inhibition of platelet adhesion to fibronectin, fibrinogen and von Willebrand factor substrates by a synthetic tetrapeptide derived from the cell-binding domain of fibronectin. *Blood* 66, 946–952

32. Burger, S. R., Zutter, M. M., Sturgill-Koszycki, S., and Santoro, S. A. (1992) Induced cell surface expression of functional $a_2b_1$ integrin during megakaryocytic differentiation of K562 leukemic cells. *Exp Cell Res* 202, 28–35.

33. Tetteroo, P. A. T., Massaro, F., Mulder, A., Schreuder-van Gelder, R., and von dem Borne, A. E. G. (1984) Megakaryocytic differentiation of proerythroblastic K562 cell-line cells. *Leukemia Res* 8, 197–206.

34. Drake, S. L., Klein, D. J., Mickelson, D. J., Oegema, T. R., Furcht, L. T., and McCarthy, J. B. (1992) Cell surface phosphotidylinosotol anchored heparan sulfate derived proteoglycan initiates mouse melanoma cell adhesion to fibronectin derived heparin binding synthetic peptides. *J Cell Biol* 117, 1331–1341.

What is claimed:

1. A peptide selected from the group consisting of SEQ ID NO:1 and fragments thereof containing the minimal sequence of SEQ ID NO:2.

2. The peptide of claim 1 consisting of the peptide sequence

```
Thr Ala Val Thr Gln Thr Tyr Gly Gly Asn Ser Asn Gly Glu Pro. [SEQ ID NO:1]
1               5                   10                  15
```

3. The peptide of claim 1 consisting of the peptide sequence

```
Thr Ala Val Thr Gln Thr Tyr. [SEQ ID NO:2]
1               5
```

4. The peptide of claim 1 consisting of the peptide sequence

```
Thr Ala Val Thr Gln Thr Tyr Gly. [SEQ ID NO:3]
1               5
```

5. The peptide of claim 1 consisting of the peptide sequence

```
Thr Ala Val Thr Gln Thr Tyr Gly Gly. [SEQ ID NO:4]
1               5
```

6. The peptide of claim 1 consisting of the peptide sequence

Thr Ala Val Thr Gln Thr Tyr Gly Gly Asn. [SEQ ID NO:5]
1           5                   10

7. The peptide of claim 1 consisting of the peptide sequence

Thr Ala Val Thr Gln Thr Tyr Gly Gly Asn Ser. [SEQ ID NO:6]
1           5                   10

8. The peptide of claim 1 consisting of the peptide sequence

Thr Ala Val Thr Gln Thr Tyr Gly Gly Asn Ser Asn. [SEQ ID NO:7]
1           5                   10

9. The peptide of claim 1 consisting of the peptide sequence

Thr Ala Val Thr Gln Thr Tyr Gly Gly Asn Ser Asn Gly. [SEQ ID NO:8]
1           5                   10

10. The peptide of claim 1 consisting of the peptide sequence

Thr Ala Val Thr Gln Thr Tyr Gly Gly Asn Ser Asn Gly Glu. [SEQ ID NO:9]
1           5                   10

* * * * *

SEQUENCE LISTING (1) GENERAL INFORMATION:

(iii) NUMBER OF SEQUENCES: 26

(2) INFORMATION FOR SEQ ID NO:1:

(i) SEQUENCE CHARACTERISTICS:
        (A) LENGTH: 15 amino acids
        (B) TYPE: amino acid
        (C) TOPOLOGY: linear (ii) MOLECULE TYPE: peptide (xi) SEQUENCE DESCRIPTION: SEQ ID NO:1:

Thr Ala Val Thr Gln Thr Tyr Gly Gly Asn Ser Asn Gly Glu Pro
    1               5                   10                  15

(2) INFORMATION FOR SEQ ID NO:2:

(i) SEQUENCE CHARACTERISTICS:
        (A) LENGTH:  7 amino acids
        (B) TYPE: amino acid
        (C) TOPOLOGY: linear (ii) MOLECULE TYPE: peptide (xi) SEQUENCE DESCRIPTION: SEQ ID NO:2:

Thr Ala Val Thr Gln Thr Tyr
    1               5

(2) INFORMATION FOR SEQ ID NO:3:

(i) SEQUENCE CHARACTERISTICS:
        (A) LENGTH: 8 amino acids
        (B) TYPE: amino acid
        (C) TOPOLOGY: linear (ii) MOLECULE TYPE: peptide (xi) SEQUENCE DESCRIPTION: SEQ ID NO:3:

Thr Ala Val Thr Gln Thr Tyr Gly
    1               5

(2) INFORMATION FOR SEQ ID NO:4:

(i) SEQUENCE CHARACTERISTICS:
        (A) LENGTH: 9 amino acids
        (B) TYPE: amino acid
        (C) TOPOLOGY: linear (ii) MOLECULE TYPE: peptide (xi) SEQUENCE DESCRIPTION: SEQ ID NO:4:

Thr Ala Val Thr Gln Thr Tyr Gly Gly
    1               5

(2) INFORMATION FOR SEQ ID NO:5:

(i) SEQUENCE CHARACTERISTICS:
        (A) LENGTH: 10 amino acids
        (B) TYPE: amino acid
        (C) TOPOLOGY: linear (ii) MOLECULE TYPE: peptide (xi) SEQUENCE DESCRIPTION: SEQ ID NO:5:

Thr Ala Val Thr Gln Thr Tyr Gly Gly Asn

```
                  1               5                    10
```

(2) INFORMATION FOR SEQ ID NO:6:

(i) SEQUENCE CHARACTERISTICS:
        (A) LENGTH: 11 amino acids
        (B) TYPE: amino acid
        (C) TOPOLOGY: linear (ii) MOLECULE TYPE: peptide (xi) SEQUENCE DESCRIPTION: SEQ ID NO:6:

```
Thr Ala Val Thr Gln Thr Tyr Gly Gly Asn Ser
1               5                   10
```

(2) INFORMATION FOR SEQ ID NO:7:

(i) SEQUENCE CHARACTERISTICS:
        (A) LENGTH: 12 amino acids
        (B) TYPE: amino acid
        (C) TOPOLOGY: linear (ii) MOLECULE TYPE: peptide (xi) SEQUENCE DESCRIPTION: SEQ ID NO:7:

```
Thr Ala Val Thr Gln Thr Tyr Gly Gly Asn Ser Asn
1               5                   10
```

(2) INFORMATION FOR SEQ ID NO:8:

(i) SEQUENCE CHARACTERISTICS:
        (A) LENGTH: 13 amino acids
        (B) TYPE: amino acid
        (C) TOPOLOGY: linear (ii) MOLECULE TYPE: peptide (xi) SEQUENCE DESCRIPTION: SEQ ID NO:8:

```
Thr Ala Val Thr Gln Thr Tyr Gly Gly Asn Ser Asn Gly
1               5                   10
```

(2) INFORMATION FOR SEQ ID NO:9:

(i) SEQUENCE CHARACTERISTICS:
        (A) LENGTH: 14 amino acids
        (B) TYPE: amino acid
        (C) TOPOLOGY: linear (ii) MOLECULE TYPE: peptide (xi) SEQUENCE DESCRIPTION: SEQ ID NO:9:

```
Thr Ala Val Thr Gln Thr Tyr Gly Gly Asn Ser Asn Gly Glu
1               5                   10
```

(2) INFORMATION FOR SEQ ID NO:10:

(i) SEQUENCE CHARACTERISTICS:
        (A) LENGTH: 8 amino acids
        (B) TYPE: amino acid
        (C) TOPOLOGY: linear (ii) MOLECULE TYPE: peptide (xi) SEQUENCE DESCRIPTION: SEQ ID NO:10:

```
Gly Gly Asn Ser Asn Gly Glu Pro
1               5
```

(2) INFORMATION FOR SEQ ID NO:11:

```
     (i) SEQUENCE CHARACTERISTICS:
         (A) LENGTH: 11 amino acids
         (B) TYPE: amino acid
         (C) TOPOLOGY: linear (ii) MOLECULE TYPE: peptide (xi) SEQUENCE DESCRIPTION: SEQ ID NO:11:

Ala Val Tyr Gln Pro Gln Pro His Pro Gln Pro
  1               5                  10

(2) INFORMATION FOR SEQ ID NO:12:

(i) SEQUENCE CHARACTERISTICS:
         (A) LENGTH: 11 amino acids
         (B) TYPE: amino acid
         (C) TOPOLOGY: linear (ii) MOLECULE TYPE: peptide (xi) SEQUENCE DESCRIPTION: SEQ ID NO:12:

Gln Met Leu Cys Thr Cys Leu Gly Asn Gly Val
  1               5                  10

(2) INFORMATION FOR SEQ ID NO:13:

(i) SEQUENCE CHARACTERISTICS:
         (A) LENGTH: 4 amino acids
         (B) TYPE: amino acid
         (C) TOPOLOGY: linear (ii) MOLECULE TYPE: peptide (xi) SEQUENCE DESCRIPTION: SEQ ID NO:13:

Thr Ala Val Thr
  1

(2) INFORMATION FOR SEQ ID NO:14:

(i) SEQUENCE CHARACTERISTICS:
         (A) LENGTH: 5 amino acids
         (B) TYPE: amino acid
         (C) TOPOLOGY: linear (ii) MOLECULE TYPE: peptide (xi) SEQUENCE DESCRIPTION: SEQ ID NO:14:

Gly Gly Asn Ser Asn
  1               5

(2) INFORMATION FOR SEQ ID NO:15:

(i) SEQUENCE CHARACTERISTICS:
         (A) LENGTH: 18 amino acids
         (B) TYPE: amino acid
         (C) TOPOLOGY: linear (ii) MOLECULE TYPE: peptide (xi) SEQUENCE DESCRIPTION: SEQ ID NO:15:

Gln Thr Tyr Gly Gly Asn Ser Asn Gly Glu Pro Ser Val Leu Pro
  1               5                  10                  15

Phe Thr Tyr (2) INFORMATION FOR SEQ ID NO:16:

(i) SEQUENCE CHARACTERISTICS:
         (A) LENGTH: 17 amino acids
         (B) TYPE: amino acid
```

(C) TOPOLOGY: linear (ii) MOLECULE TYPE: peptide (xi) SEQUENCE DESCRIPTION: SEQ ID NO:16:

Ala Ala Val Tyr Gln Pro Gln Pro His Pro Gln Pro Pro Pro Tyr
1               5                   10                  15

Gly His (2) INFORMATION FOR SEQ ID NO:17:

(i) SEQUENCE CHARACTERISTICS:
        (A) LENGTH: 37 amino acids
        (B) TYPE: amino acid
        (C) TOPOLOGY: linear (ii) MOLECULE TYPE: peptide (xi) SEQUENCE DESCRIPTION: SEQ ID NO:17:

Cys Val Thr Asp Ser Gly Val Val Tyr Ser Val Gly Met Gln Trp
1               5                   10                  15

Leu Lys Thr Gln Gly Asn Lys Gln Met Leu Cys Thr Cys Leu Gly
                20                  25                  30

Asn Gly Val Ser Cys Gln Glu
                35

(2) INFORMATION FOR SEQ ID NO:18:

(i) SEQUENCE CHARACTERISTICS:
        (A) LENGTH: 60 amino acids
        (B) TYPE: amino acid
        (C) TOPOLOGY: linear (ii) MOLECULE TYPE: peptide (xi) SEQUENCE DESCRIPTION: SEQ ID NO:18:

Thr Ala Val Thr Gln Thr Tyr Gly Gly Asn Ser Asn Gly Glu Pro
1               5                   10                  15

Cys Val Leu Pro Phe Thr Tyr Asn Gly Arg Thr Phe Tyr Ser Cys
                20                  25                  30

Thr Thr Glu Gly Arg Gln Asp Gly His Leu Trp Cys Ser Thr Thr
                35                  40                  45

Ser Asn Tyr Glu Gln Asp Gln Lys Tyr Ser Phe Cys Thr Asp His
                50                  55                  60

(2) INFORMATION FOR SEQ ID NO:19:

(i) SEQUENCE CHARACTERISTICS:
        (A) LENGTH: 65 amino acids
        (B) TYPE: amino acid
        (C) TOPOLOGY: linear (ii) MOLECULE TYPE: peptide (xi) SEQUENCE DESCRIPTION: SEQ ID NO:19:

Thr Val Leu Val Gln Thr Gln Gly Gly Asn Ser Asn Gly Ala Leu
1               5                   10                  15

Cys His Phe Pro Phe Leu Tyr Asn Asn His Asn Tyr Thr Asp Cys
                20                  25                  30

Thr Ser Glu Gly Arg Arg Asp Asn Met Lys Trp Cys Gly Thr Thr
                35                  40                  45

Gln Asn Tyr Asp Ala Asp Gln Lys Phe Gly Phe Cys Pro Met Ala
                50                  55                  60

```
    Ala His Glu Glu Ile
                65

(2) INFORMATION FOR SEQ ID NO:20:

(i) SEQUENCE CHARACTERISTICS:
        (A) LENGTH: 48 amino acids
        (B) TYPE: amino acid
        (C) TOPOLOGY: linear (ii) MOLECULE TYPE: peptide (xi) SEQUENCE DESCRIPTION: SEQ ID NO:20:

Cys Thr Thr Asn Glu Gly Val Met Tyr Arg Ile Gly Asp Gln Trp
                     5                  10                  15

Asp Lys Gln His Asp Met Gly His Met Met Arg Cys Thr Cys Val
                    20                  25                  30

Gly Asn Gly Arg Gly Glu Trp Thr Cys Tyr Ala Tyr Ser Gln Leu
                    35                  40                  45

Arg Asp Gln (2) INFORMATION FOR SEQ ID NO:21:

(i) SEQUENCE CHARACTERISTICS:
        (A) LENGTH: 43 amino acids
        (B) TYPE: amino acid
        (C) TOPOLOGY: linear (ii) MOLECULE TYPE: peptide (xi) SEQUENCE DESCRIPTION: SEQ ID NO:21:

Cys Ile Val Asp Asp Ile Thr Tyr Asn Val Asn Asp Thr Phe His
    1                5                  10                  15

Lys Arg His Glu Glu Gly His Met Leu Asn Cys Thr Cys Phe Gly
                    20                  25                  30

Gln Gly Arg Gly Arg Trp Lys Cys Asp Pro Val Asp Gln
                    35                  40

(2) INFORMATION FOR SEQ ID NO:22:

(i) SEQUENCE CHARACTERISTICS:
        (A) LENGTH:  48 amino acids
        (B) TYPE: amino acid
        (C) TOPOLOGY: linear (ii) MOLECULE TYPE: peptide (xi) SEQUENCE DESCRIPTION: SEQ ID NO:22:

Cys Gln Asp Ser Glu Thr Gly Thr Phe Tyr Gln Ile Gly Asp Ser
    1                5                  10                  15

Trp Glu Lys Tyr Val His Gly Val Arg Tyr Gln Cys Tyr Cys Tyr
                    20                  25                  30

Gly Arg Gly Ile Gly Glu Trp His Cys Gln Pro Leu Gln Thr Tyr
                    35                  40                  45

Pro Ser Ser (2) INFORMATION FOR SEQ ID NO:23:

(i) SEQUENCE CHARACTERISTICS:
        (A) LENGTH: 24 amino acids
        (B) TYPE: amino acid
        (C) TOPOLOGY: linear (ii) MOLECULE TYPE: peptide
```

```
(xi) SEQUENCE DESCRIPTION: SEQ ID NO:23:

Gln Thr Tyr Gly Gly Asn Ser Asn Gly Glu Pro Ser Val Leu Pro
1               5                   10                  15

Phe Thr Tyr Asn Gly Arg Thr Phe Tyr
                20

(2) INFORMATION FOR SEQ ID NO:24:

(i) SEQUENCE CHARACTERISTICS:
        (A) LENGTH: 17 amino acids
        (B) TYPE: amino acid
        (C) TOPOLOGY: linear (ii) MOLECULE TYPE: peptide (xi) SEQUENCE DESCRIPTION: SEQ ID NO:24:

Pro Phe Thr Tyr Asn Gly Arg Thr Phe Tyr Ser Ser Thr Thr Glu
1               5                   10                  15

Gly Arg (2) INFORMATION FOR SEQ ID NO:25:

(i) SEQUENCE CHARACTERISTICS:
        (A) LENGTH: 12 amino acids
        (B) TYPE: amino acid
        (C) TOPOLOGY: linear (ii) MOLECULE TYPE: peptide (xi) SEQUENCE DESCRIPTION: SEQ ID NO:25:

Thr Thr Glu Gly Arg Gln Asp Gly His Leu Trp Ser
1               5                   10

(2) INFORMATION FOR SEQ ID NO:26:

(i) SEQUENCE CHARACTERISTICS:
        (A) LENGTH: 16 amino acids
        (B) TYPE: amino acid
        (C) TOPOLOGY: linear (ii) MOLECULE TYPE: peptide (xi) SEQUENCE DESCRIPTION: SEQ ID NO:26:

Ser Ser Thr Thr Ser Asn Tyr Glu Gln Asp Gln Lys Tyr Ser Phe
1               5                   10                  15

Ser
```